United States Patent
Koehler et al.

(10) Patent No.: US 10,568,588 B2
(45) Date of Patent: Feb. 25, 2020

(54) TILED DETECTOR ARRANGEMENT FOR DIFFERENTIAL PHASE CONTRAST CT

(71) Applicant: KONINKLIJKE PHILIPS N.V., Eindhoven (NL)

(72) Inventors: Thomas Koehler, Hamburg (DE); Franz Pfeiffer, Unterföhring (DE); Peter Benjamin Theodor Noel, Unterföhring (DE); Dieter Richard Hahn, Memmelsdorf (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 144 days.

(21) Appl. No.: 15/580,341

(22) PCT Filed: Jun. 10, 2016

(86) PCT No.: PCT/EP2016/063235
§ 371 (c)(1),
(2) Date: Dec. 7, 2017

(87) PCT Pub. No.: WO2016/202685
PCT Pub. Date: Dec. 22, 2016

(65) Prior Publication Data
US 2018/0192967 A1    Jul. 12, 2018

(30) Foreign Application Priority Data
Jun. 15, 2015  (EP) .................................... 15172007

(51) Int. Cl.
*G03G 13/05*    (2006.01)
*A61B 6/03*     (2006.01)
*A61B 6/00*     (2006.01)
*G01N 23/046*   (2018.01)

(52) U.S. Cl.
CPC .............. *A61B 6/035* (2013.01); *A61B 6/032* (2013.01); *A61B 6/4233* (2013.01); *A61B 6/4291* (2013.01); *A61B 6/463* (2013.01); *A61B 6/465* (2013.01); *A61B 6/467* (2013.01);
(Continued)

(58) Field of Classification Search
CPC ......... A61B 6/463; A61B 6/465; A61B 6/467; A61B 6/587; A61B 6/035; A61B 6/032; A61B 6/4233; A61B 6/4291; A61B 6/484; A61B 6/5205; G01N 23/046; G01N 2223/419
See application file for complete search history.

(56) References Cited

U.S. PATENT DOCUMENTS

| 5,164,973 A | 11/1992 | Takahashi |
| 2007/0081624 A1* | 4/2007 | Nabatame ............... A61B 6/032 378/19 |

(Continued)

FOREIGN PATENT DOCUMENTS

| JP | 3583567 B2 | 11/2004 |
| WO | 2011070493 A1 | 6/2011 |

*Primary Examiner* — Kiho Kim
(74) *Attorney, Agent, or Firm* — Larry Liberchuk

(57) ABSTRACT

Radiation source and detector arrangement for a differential phase contrast CT scanner, in which the detector tiles are placed asymmetrically such that direct rays, which hit gaps between tiles are sampled by tile centers for the complementary rays. This may provide for good image quality without any approximate processing.

11 Claims, 3 Drawing Sheets

(52) U.S. Cl.
CPC ............ *A61B 6/484* (2013.01); *A61B 6/5205* (2013.01); *G01N 23/046* (2013.01); *G01N 2223/419* (2013.01)

(56) References Cited

U.S. PATENT DOCUMENTS

| | | | |
|---|---|---|---|
| 2007/0183560 A1* | 8/2007 | Popescu | A61B 6/032 378/5 |
| 2007/0183562 A1* | 8/2007 | Popescu | A61B 6/032 378/19 |
| 2008/0061395 A1 | 3/2008 | Tkaczyk | |
| 2012/0307966 A1* | 12/2012 | Roessl | A61B 6/00 378/16 |
| 2014/0177795 A1 | 6/2014 | Spahn | |

* cited by examiner

TILED DETECTOR ARRANGEMENT FOR DIFFERENTIAL PHASE CONTRAST CT

CROSS-REFERENCE TO PRIOR APPLICATIONS

This application is the U.S. National Phase application under 35 U.S.C. § 371 of International Application No. PCT/EP2016/063235, filed on Jun. 10, 2016, which claims the benefit of European Patent Application No. 15172007.5, filed on Jun. 15, 2015. These applications are hereby incorporated by reference herein.

FIELD OF THE INVENTION

The invention relates to the field of differential phase contrast and dark-field computed tomography. In particular, the invention relates to a rotating radiation source and detector arrangement for a differential phase contrast and/or dark-field computed tomography scanner, a computed tomography examination apparatus, a method of acquiring an image of an object of interest with a differential phase contrast computed tomography scanner or a dark-field computed tomography scanner, a program element and a computer-readable medium.

BACKGROUND OF THE INVENTION

While classical X-ray imaging measures absorption of X-rays caused by an object, phase contrast imaging aims at a detection of a phase shift X-rays are subjected to when they pass through an object to be examined. For phase contrast imaging and/or dark-field imaging, an interferometer (e.g. a grating) is placed behind the object to generate an interference pattern of intensity maxima and minima when the object is irradiated with (coherent) X-rays. Any phase shift in the X-ray waves that is introduced by the object causes some characteristic displacement in the interference pattern. Measuring these displacements therefore allows reconstructing the phase shift of the object. In addition, when employing such interferometer, the generation of image data deriving from de-coherent X-ray small angle scattering is enabled. The latter type of imaging is also referred to as "dark-field imaging".

A grating based phase contrast computed tomography scanner for medical applications comprises a plurality of detector tiles. Each detector tile comprises an interferometer and a radiation detector element. Such a detector may also be called a tiled detector.

Tiling, however, implies that there may be gaps between adjacent tiles. In particular, in case of phase contrast CT systems, the tiling may be a challenge to image quality, at least for two reasons: Firstly, if differential data are acquired the interpolation of data across gaps between tiles may be even more critical than for standard, non-differential data. Secondly, each tile may comprise two gratings and a radiation detector and has a depth of a couple of centimeters, which is defined by the Talbot distance of the interferometer. This condition may increase the gaps even further.

U.S. Pat. No. 5,164,973 A1 describes a projection detecting apparatus for computed tomography, which includes a tiled detector.

SUMMARY OF THE INVENTION

It may be desirable to provide for good image quality for tiled detectors in an efficient manner.

Aspects of the invention are stated in the independent claims. Advantages and further embodiments are set out in the dependent claims, the description and the figures.

A first aspect of the invention relates to a rotating radiation source and detector arrangement for a differential phase contrast and/or dark-field computed tomography scanner. The radiation source and detector arrangement comprises a radiation source and a detector.

The detector comprises a plurality of detector tiles, wherein each detector tile comprises an interferometer and a radiation detector element. The detector tiles are arranged along a circular arc and asymmetrical relative to a line, which passes through the position of the radiation source and the center of rotation of the arrangement.

The circular arc along which the detector tiles are arranged may have a center coinciding with the position of the radiation source.

In other words, the detector tiles are placed asymmetrically, such that radiation emitted by the radiation source along a first line, which runs towards the detector, may hit a gap between two adjacent tiles. However, if the radiation source and detector arrangement is rotated, such that the source is positioned on the first line but on the other side of the object of interest, and emits radiation along the first line, but in opposite direction, the radiation does not hit a gap between two adjacent tiles, but hits a tile close to its center or, for example, a quarter width of the tile offset the center. Thus, the complementary radiation, also called complementary ray, can be detected by the tile and used for image generation.

Therefore, data of direct rays, which hit gaps between tiles, can be sampled by complementary data of complementary rays, which hit a tile, or in other words, complementary rays are used to close the "data gap" of the image data corresponding to the direct rays.

According to an exemplary embodiment, a first tile of the plurality of detector tiles is arranged with a quarter tile offset with respect to the line which passes through the position of the radiation source and the center of rotation of the arrangement.

Each interferometer of each detector tile of the plurality of detector tiles may comprise a phase grating. Also, each interferometer of each detector tile of the plurality of detector tiles may comprise an analyzer grating.

Further, the radiation source may comprise a source grating. Advantageously, the arrangement may be less susceptible to generate ring artifacts in the reconstructed images.

Another aspect of the invention relates to a computed tomography examination apparatus, which comprise the above and below described arrangement of a rotating radiation source and detector.

The computed tomography examination apparatus may be a single slice CT system or a cone-beam CT system.

According to another aspect of the invention, a method of acquiring an image of an object of interest with a differential phase contrast computed tomography scanner or a dark-field computed tomography scanner is provided, in which a radiation source emits a first beam of electromagnetic radiation along a first path in a first direction towards a detector, the detector having a plurality of detector tiles, wherein the first path hits a gap between two adjacent tiles. Then, the radiation source and the detector arrangement are rotated and the radiation source emits then a second, complementary beam of electromagnetic radiation along a second path in a second direction towards the detector. The first path equals the second path and the first direction is opposite the second direction. The detector tiles are arranged in such a way that the second path hits a tile and not a gap between two adjacent tiles of the detector.

The data detected by the detector and which corresponds to the second beam is used for image reconstruction. The "complementary data" is used for filling the "data gap" caused by the gaps between adjacent tiles, when the first beam of electromagnetic radiation hits the gap between the two adjacent tiles. In other words, data acquired while the X-ray source is on the opposite side of the object of interest is used to fill data gaps caused by gaps between adjacent tiles when the X-ray source was on the initial side of the object of interest, i.e., opposite to the opposite side.

Another aspect of the invention relates to a program element, which, when being executed by a processor of a computed tomography examination apparatus or a dark-field computed tomography scanner, instructs the apparatus (or scanner) to carry out the above and/or below described method steps.

Another aspect of the invention relates to a computer-readable medium, on which the above described program element is stored.

The computer-readable medium may be a floppy disk, a hard disk, a CD, a DVD, an USB (Universal Serial Bus) storage device, a RAM (Random Access Memory), a ROM (Read Only Memory) and an EPROM (Erasable Programmable Read Only Memory). A computer-readable medium may also be a data communication network, for example the Internet, which allows downloading a program code.

The present invention allows for useful application in a clinical environment such as a hospital. More specifically, the present invention is very suitable for medical examination of patients. In addition, the presentation invention allows for useful application in an industrial environment. More specifically, the present invention is very suitable for application in non-destructive testing (e.g. analysis as to composition, structure and/or qualities of biological as well non-biological samples) as well as security scanning (e.g. scanning of luggage on airports).

These and other aspects of the invention will be apparent from and elucidated with reference to the embodiments described hereinafter. Exemplary embodiments of the present invention will now be described in the following, with reference to the following drawings.

BRIEF DESCRIPTION OF THE DRAWINGS

The figures are schematic and not true to scale. If the same reference signs are used in different figures, they may refer to identical or similar elements. However, identical or similar elements may also be labeled with different reference signs.

DETAILED DESCRIPTION OF EMBODIMENTS

Figure 1:
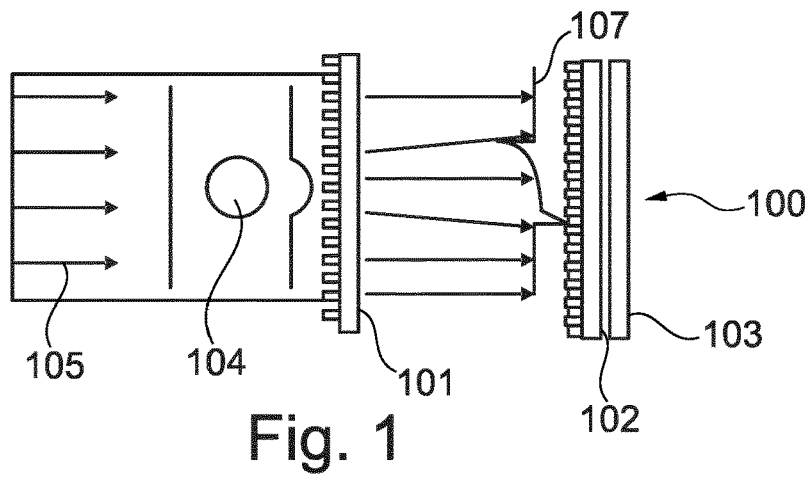
FIG. 1 shows a partial view of a rotating radiation source and detector arrangement according to an exemplary embodiment of the invention.

FIG. 1 shows a detector tile 100 of a radiation source and detector arrangement for a differential phase contrast and/or dark-field computed tomography scanner according to an exemplary embodiment of the invention. The arrangement comprises a radiation source (not shown), which emits electromagnetic radiation (X-rays) towards an object of interest 104.

During operation, Before the X-rays 105 impact on the object of interest 104, they may pass a source grating. After passing the object of interest 104, the X-rays reach the detector 300. The detector 300 in this specific example comprises a phase grating 101. The detector 300 in this specific example furthermore comprises an analyzer grating 102 for analyzing the interference pattern 107 produced by the phase grating 101. Alternatively, the radiation detector 103 has a pitch sufficiently small, hence a spatial resolution sufficiently large, for detecting i.e. adequately resolving the interference pattern generated by the phase grating 101, thereby omitting the need for the analyzer grating 102. For that purpose the radiation detector 103 unit may be a high resolution X-ray detector known per se having a spatial resolution of 50 micrometers or more, or an X-ray detector of the type as described in US 2014/0177795 A1 which is incorporated herein by reference. Downstream the analyzer grating 102, seen in the direction of the X-rays 105, a radiation detector 103 is arranged.

The arrangement is designed to rotate around a center of rotation, which, in the typical case, coincides with the position of the object of interest 104.

Figure 2A:
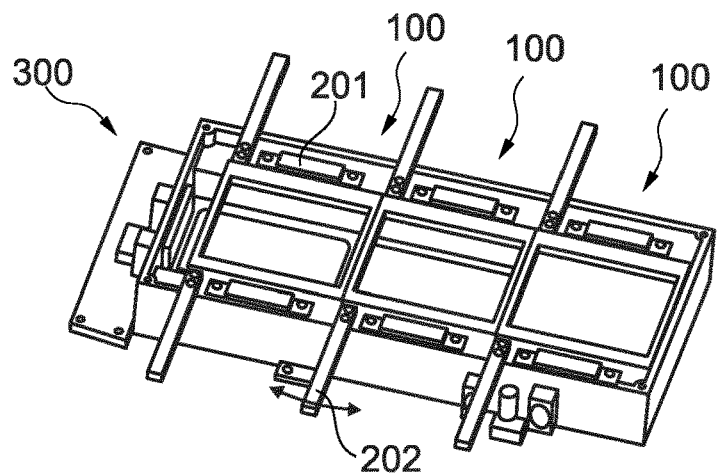
FIG. 2A shows a large area interferometer comprising three grating pairs.

FIG. 2A shows a detector 300 with three detector tiles, each detector tile comprising a phase grating and an analyzer grating. Each detector tile is attached to a pivot bearing 201, which pivotally attaches the tile to the frame of the detector 300. Further, each tile may comprise an actuator lever arm 202 for adjusting the position and orientation of the tile.

Figure 2B:
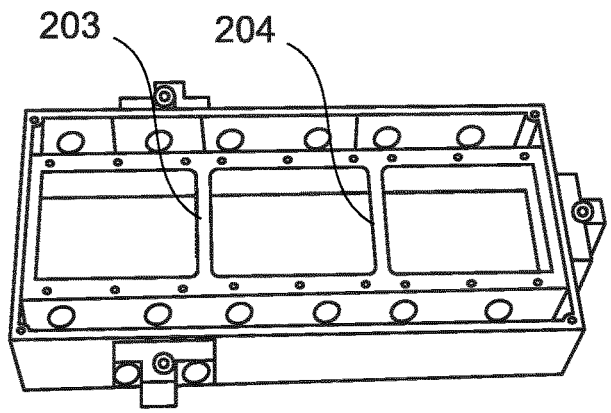
FIG. 2B shows a frame of the large area interferometer of FIG. 2A.

FIG. 2B shows a frame of the detector 300 of FIG. 2A. As can be seen from FIGS. 2A and 2B, there are gaps 203, 204 between adjacent grating pairs which may be considered as "blind spots", i.e., incapable of detecting radiation.

Figure 3A:
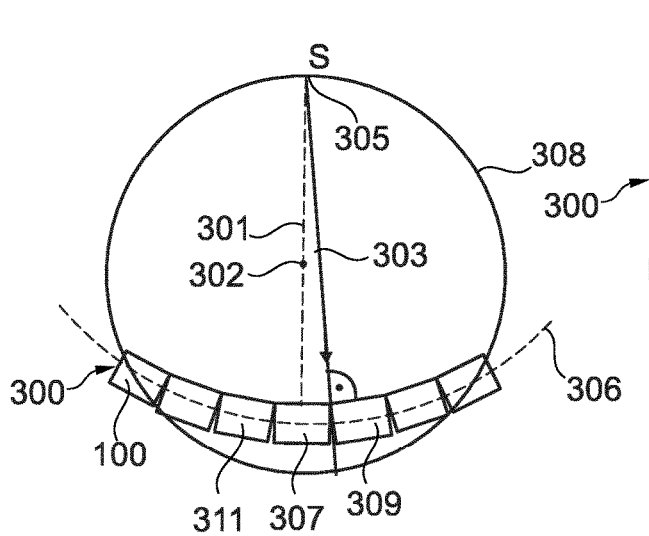
FIG. 3A shows a radiation source and detector arrangement in a first position.
Figure 3B:
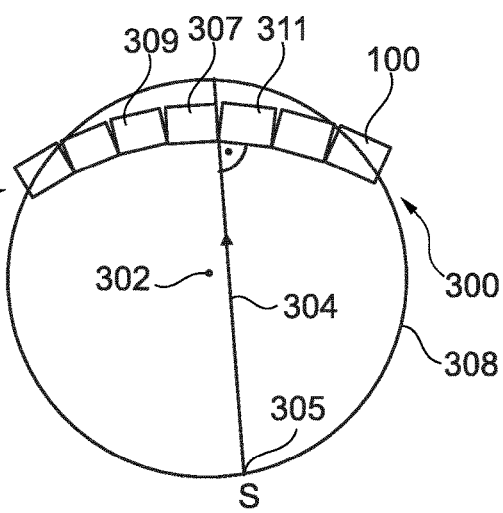
FIG. 3B shows a radiation source and detector arrangement of FIG. 3A in a second, complementary position.

FIG. 3A shows a rotating radiation source 305 and detector 300 arrangement for a differential phase contrast and/or dark-field computed tomography scanner. The detector 300 comprises a plurality of detector tiles 100, 307, 309, which are arranged along a circular arc 306 around the radiation source 305. The radiation source 305 and the detector 300 rotate around center 302 along a circular path 308. The detector tiles 100, 307 are arranged symmetrical to a line 301, which passes through the position of the radiation source 305 and the center of rotation 302. A beam of radiation emitted by the source along path 303 towards the detector hits a gap between two adjacent tiles 307, 309. If the radiation source and the detector are rotated to a position in which the source can emit radiation along the same path 303, but in opposite direction (this radiation beam is also called a complementary way), the radiation hits again a gap between adjacent tiles 307, 311.

It should be noted that the technique of placing detector panels asymmetrically to the center of rotation 302 is applicable to flat-panel type detectors in CT systems, as well as detectors arranged on a circular arc, as illustrated in FIG. 3A. Therefore, it will be appreciated that the placement of detectors on a circular arc is not essential.

Figure 4A:
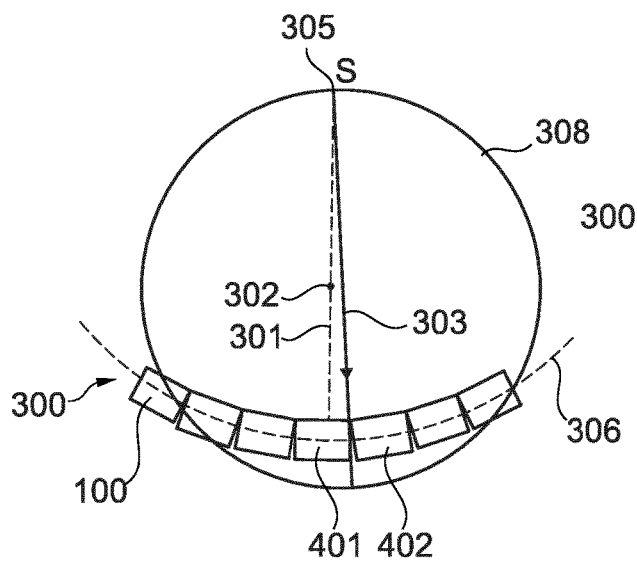
FIG. 4A shows a radiation source and detector arrangement according to an exemplary embodiment of the invention.
Figure 4B:
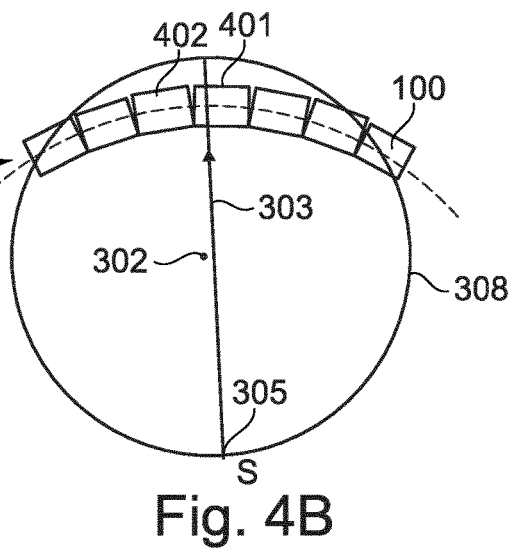
FIG. 4B shows the radiation source and detector arrangement of FIG. 4A in a second, complementary position.

FIGS. 4A and 4B show a rotating radiation source and detector 300 arrangement according to an exemplary embodiment of the invention. The tiles 100, 401, etc. are arranged asymmetrically relative to the line 301, such that the ray hits the gap between the adjacent tiles 401, 402, when the source is in the position depicted in FIG. 4A. However, in the position of FIG. 4B, in which the source is on the opposite side of the object of interest (which is not depicted in FIGS. 4A, 4B, but arranged in the circle 308, such that detector and source can rotate around the object of interest), the path 303 does not hit a gap but hits the tile 401. The detector tiles are placed asymmetrically, for example with a quarter tile offset to line 301, such that direct rays, which hit gaps between adjacent tiles, are sampled by tile centers for the complementary rays.

For a single slice CT system, direct data and complementary data can be combined in order to fill the gaps between tiles and simple filtered back-projection can be used for reconstruction. For a cone-beam system, a way to reconstruct images from a tiled system with gaps is to use iterative reconstruction methods. Since iterative reconstruction may use all acquired data properly, there may be no need to interleave direct and complementary rays explicitly. Thus, the benefit of the interleaved placement of gaps in direct and complementary projections may be exploited without any additional and approximate processing.

Figure 5:
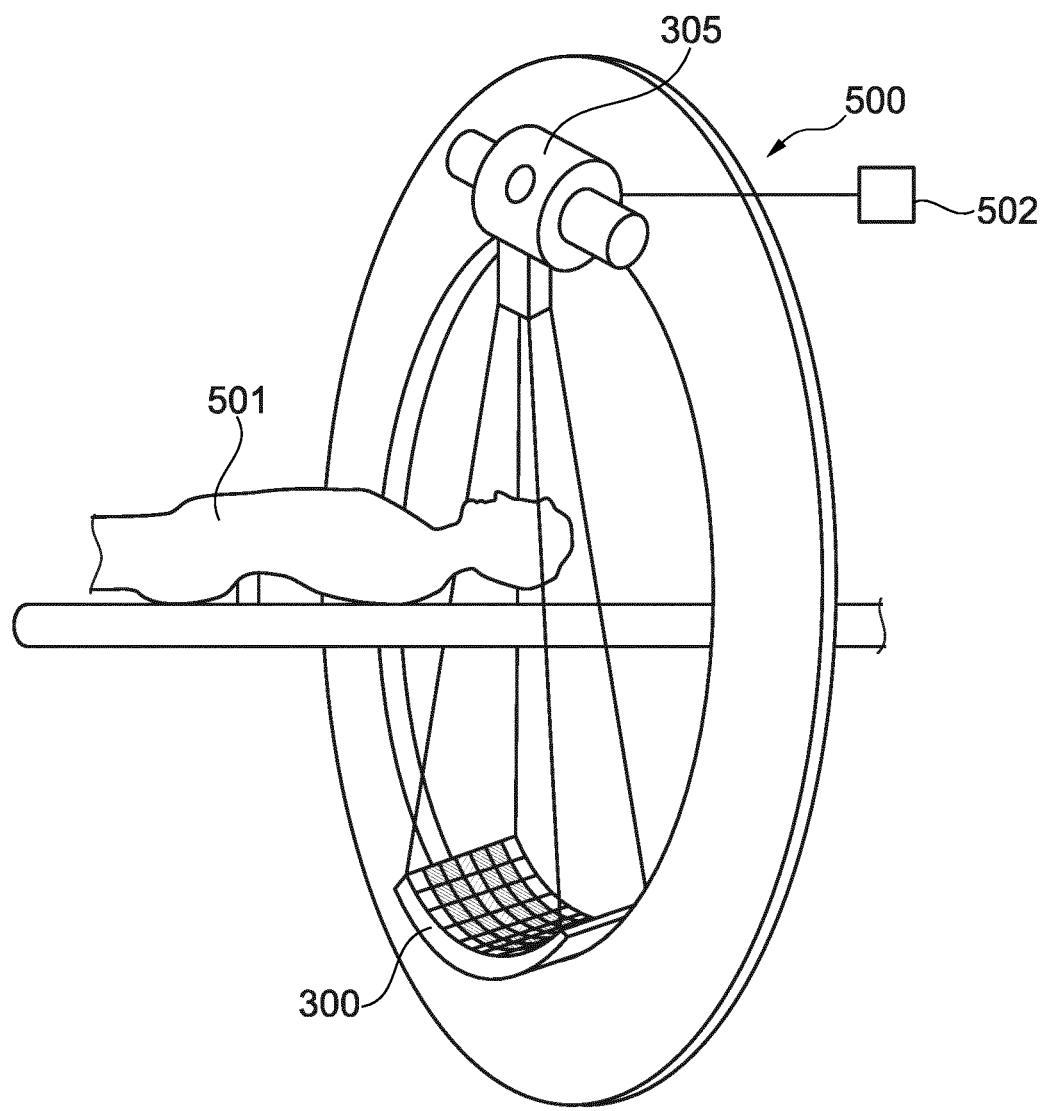
FIG. 5 shows an examination apparatus according to an exemplary embodiment of the invention.

FIG. 5 shows a computed tomography examination apparatus 500 comprising the above described arrangement of radiation source 305 and detector 300, rotating around an object of interest 501. The apparatus may be adapted as a medical imaging apparatus and comprises a processor 502 for controlling the operation of the apparatus and for carrying out the image generation.

Figure 6:
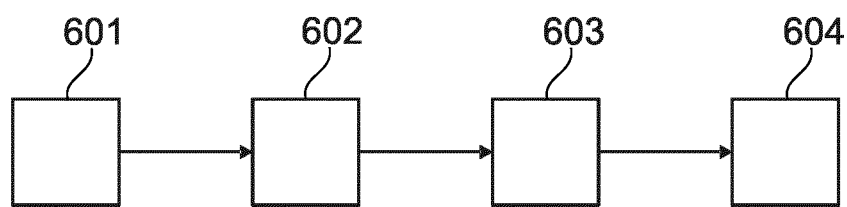
FIG. 6 shows a flow-chart of a method according to an exemplary embodiment of the invention.

FIG. 6 shows a flow-chart of a method according to an exemplary embodiment of the invention. In step 601, an X-ray radiation source emits a first beam of X-rays along first path in a first direction towards the detector, which has been described above in more detail. Both the radiation source and the detector are then rotated towards a different position, in which the source is on the opposite side of the object of interest to be examined. In step 603, the source emits a second, complementary beam of electromagnetic radiation in the opposite direction which is then detected by the detector. In step 604, the detection data which has been acquired when the source was on the opposite side of the object of interest, is used for filling the "data gap" in the detection data acquired when the source was on the initial side of the object of interest and the radiation beam has hit the gap between adjacent tiles of the detector.

It should be noted that the term "comprising" does not rule out a plurality. Let it further be noted that features described with reference to one of the above exemplary embodiments can also be used in combination with other features of other exemplary embodiments described above. Moreover, while at least one exemplary embodiment has been presented in the foregoing summary and detailed description, it should be appreciated that a vast number of variations exist. It should also be appreciated that the exemplary embodiment or exemplary embodiments are only examples, and are not intended to limit the scope, applicability, or configuration in any way. Rather, the foregoing summary and detailed description will provide those skilled in the art with a convenient road map for implementing an exemplary embodiment, it being understood that various changes may be made in the function and arrangement of elements described in an exemplary embodiment without departing from the scope as set forth in the appended claims and their legal equivalents.

The invention claimed is:

1. A differential phase contrast and/or dark-field computed tomography examination system for acquiring an image of an object of interest, the system comprising:
   a radiation source for emitting a plurality of beams of electromagnetic radiation; and
   a detector comprising a plurality of detector tiles being offset by a portion of one detector tile with respect to a central beam of the plurality of beams, each detector tile comprising an interferometer and a radiation detector;
   wherein the radiation source emits a first beam of the plurality of beams along a first path in a first direction towards the detector such that the first beam strikes a gap between two adjacent detector tiles;
   wherein when the radiation source and the detector are rotated, the radiation source emits a second beam of the plurality of beams along a second path in a second direction towards the detector such that the second beam strikes a detector tile instead of a gap between two adjacent detector tiles; and wherein the first path equals the second path and the first direction is opposite the second direction.

2. The system according to claim 1, wherein a first detector tile of the plurality of detector tiles is arranged with a quarter tile offset with respect to the central beam.

3. The system according to claim 2, wherein the first detector tile is positioned in a center of the plurality of detector tiles.

4. The system according to claim 1, wherein the interferometer of each detector tile comprises a phase grating.

5. The system according to claim 1, wherein the interferometer of each detector tile comprises an analyzer grating.

6. The system according to claim 1, wherein the radiation source comprises a source grating.

7. The system according to claim 1, wherein the detector tiles are arranged along a circular arc.

8. The system according to claim 7, wherein the circular arc has a center coinciding with the radiation source.

9. A method for acquiring an image of an object of interest in differential phase contrast and/or dark-field computed tomography, the method comprising:
   emitting a plurality of beams of electromagnetic radiation;
   providing a detector comprising a plurality of detector tiles being offset by a portion of one detector tile with respect to a central beam of the plurality of beams, each detector tile comprising an interferometer and a radiation detector;
   emitting a first beam of the plurality of beams along a first path in a first direction towards the detector such that the first beam strikes a gap between two adjacent detector tiles;
   rotating the radiation source and the detector; and
   emitting a second beam of the plurality of beams along a second path in a second direction towards the detector such that the second beam strikes a detector tile instead of a gap between two adjacent detector tiles; and wherein the first path equals the second path and the first direction is opposite the second direction.

10. The method according to claim 9, further comprising:
   using detection data corresponding to the second beam for image reconstruction.

11. A non-transitory computer-readable medium having one or more executable instructions stored thereon which, when executed by at least one processor, cause the at least one processor to perform a method for acquiring an image of an object of interest in differential phase contrast and/or dark-field computed tomography, the method comprising:

emitting a plurality of beams of electromagnetic radiation;

providing a detector comprising a plurality of detector tiles being offset by a portion of one detector tile with respect to a central beam of the plurality of beams, each detector tile comprising an interferometer and a radiation detector;

emitting a first beam of the plurality of beams along a first path in a first direction towards the detector such that the first beam strikes a gap between two adjacent detector tiles;

rotating the radiation source and the detector; and emitting a second beam of the plurality of beams along a second path in a second direction towards the detector such that the second beam strikes a detector tile instead of a gap between two adjacent detector tiles; and wherein the first path equals the second path and the first direction is opposite the second direction.

* * * * *